United States Patent [19]

Klemm

[11] Plant 5,204

[45] Mar. 13, 1984

[54] CARNATION NAMED MINTOP

[76] Inventor: Siegfried Klemm, Hanfacker 9, 7000 Stuttgart 50, Fed. Rep. of Germany

[21] Appl. No.: 401,562

[22] Filed: Jul. 26, 1982

[51] Int. Cl.[3] ..... A01H 5/00

[52] U.S. Cl. ..... Plt./70

[58] Field of Search ..... Plt./70

*Primary Examiner*—James R. Feyrer

*Attorney, Agent, or Firm*—Chas W. Rummler

[57] ABSTRACT

A new hybrid spray carnation distinguished by its profuse and continuous production of deep pink flowers of medium size, each petal of which is bordered with a ruffled white margin about 5 mm. in width, the flowers being borne singly on strong upright pedicels carried in a spray arrangement on sturdy upright peduncles about 45 cm. long.

1 Drawing Figure

BACKGROUND OF THE NEW PLANT

This new carnation originated at Stuttgart, West Germany, as a seedling derived by my crossing plants selected from breeding stock maintained in my greenhouses at Stuttgart, the object of this crossing being the production of an improved carnation suitable for cut flowers. The cross for this plant was made on Apr. 8, 1973. Asexual propagation of this new plant, by means of cuttings, has been carried out at Stuttgart by me and under my direction through successive generations and the distinctive characteristics of this plant have been found to hold true from generation to generation and appear to be firmly fixed.

DESCRIPTION OF THE DRAWING

My new variety of carnation plant is illustrated by the accompanying full color photographic drawing, which shows a group of flowering stems having buds in various stages of opening, newly opened flowers and blooms in further stages of maturity, the flower coloration being shown as nearly true as it is reasonably possible to obtain by means of conventional photographic procedures.

DESCRIPTION OF THE NEW PLANT

The following is a detailed description of my new carnation variety based upon observation of plants grown under conventional greenhouse practices, with color designations being according to The R.H.S. Colour Chart published by The Royal Horticultural Society of London, England.

THE PLANT

Origin: Seedling.
Parentage:
*Seed plant.*—Seedling No. 3675 (unpatented).
*Pollen parent.*—Seedling No. 8-74-11 (unpatented).
Classification:
*Botanic.*—*Dyanthus caryophyllus.*
*Commercial.*—Greenhouse spray carnation.
Form: Bush.
Height: From about 90 cm. to about 120 cm.
Growth: Vigorous and erect with excellent strength.
Branching: Normal.
Foliage: Quantity-— Moderate.
*Leaf size.*—Medium.

*Leaf shape.*—Oblong with entire margin.
*Texture.*—*Smooth.*
*Color.*—Upper side — Blue-Green. Under side — Blue-Green.

THE BUD

Size: Medium, about 15 mm. in diameter and about 42 mm. long.
Form: Generally ovoid with cuspidate apex.
Opening rate: Moderate.
Color:
*When sepals first divide.*—Yellow-Green.
*When petals begin to unfurl.*—Yellow-Green.
Calyx:
*Size.*—Medium, about 15 mm. broad and about 17 mm. long.
*Shape.*—Bell-shaped.
*Aspect.*—Smooth.
*Splitting.*—The calyx does not split.
Sepals:
*Condition.*—Upstanding.
*Color.*—Inside — Grey-Green. Outside — Yellow-Green.
Pedicels: Rigid and generally upright.
*Color.*—Grey-Green.
Peduncle: Rigid and erect.
*Color.*—Grey-Green.

THE FLOWER

Blooming habit: Continuous and profuse.
Size of bloom: Medium to tall.
*Diameter.*—About 65 mm.
*Depth.*—About 35–40 mm.
Borne: Singly.
Shape: High center at first opening and the form does not change as the flower matures.
Petalage: Number of petals — About 39.
*Arrangement.*—Generally imbricated.
*Form.*—Fan shaped with ruffled end margins.
*Color.*—Outer and inside petals — R.H.S. 52A in the main body, fading to 55A near the ruffled margin which becomes almost clear white. Reverse side — R.H.S. 52A to 55A.
*Texture.*—Soft.
*Appearance.*—Shiny.
Peduncle: Sturdy and upright.
*Length.*—About 45 cm.
*Color.*—Grey-Green.

Persistence: The flowers hang on and dry.
Fragrance: Weak.
Lasting quality:
*On the plant.*—About 16 days.
*As a cut flower.*—About 12 days.

REPRODUCTIVE ORGANS

Stamens: Anthers and pollen are rarely present.
Pistils: Number — Not more than 3.
*Length.*—About 40 mm.
*Stigmas.*—Color — Cream Yellow.
Fruit: Fertile.
*Shape.*—Cylindrical.
*Color.*—Greenish Brown at maturity.

This new variety of carnation plant is particularly distinguished by the bright pink coloring of its flowers which have petals with a ruffled and undulating margin, almost white in color, and which are borne on relatively long, strong pedicels. The flower has a closed calyx which does not split and the plant has an excellent capacity for continuous and profuse production of blooms which is a character of considerable merit for the cut flower market.

I claim:

1. A new and distinct varity of carnation plant, substantially as herein shown and descried, characterized by its high productivity of bright pink flowers borne singly on rigid, generally upright pedicels carried in spray arrangement on a sturdy upright peduncle, the flowers being characterized by having petals which have ruffled margins of clear white.

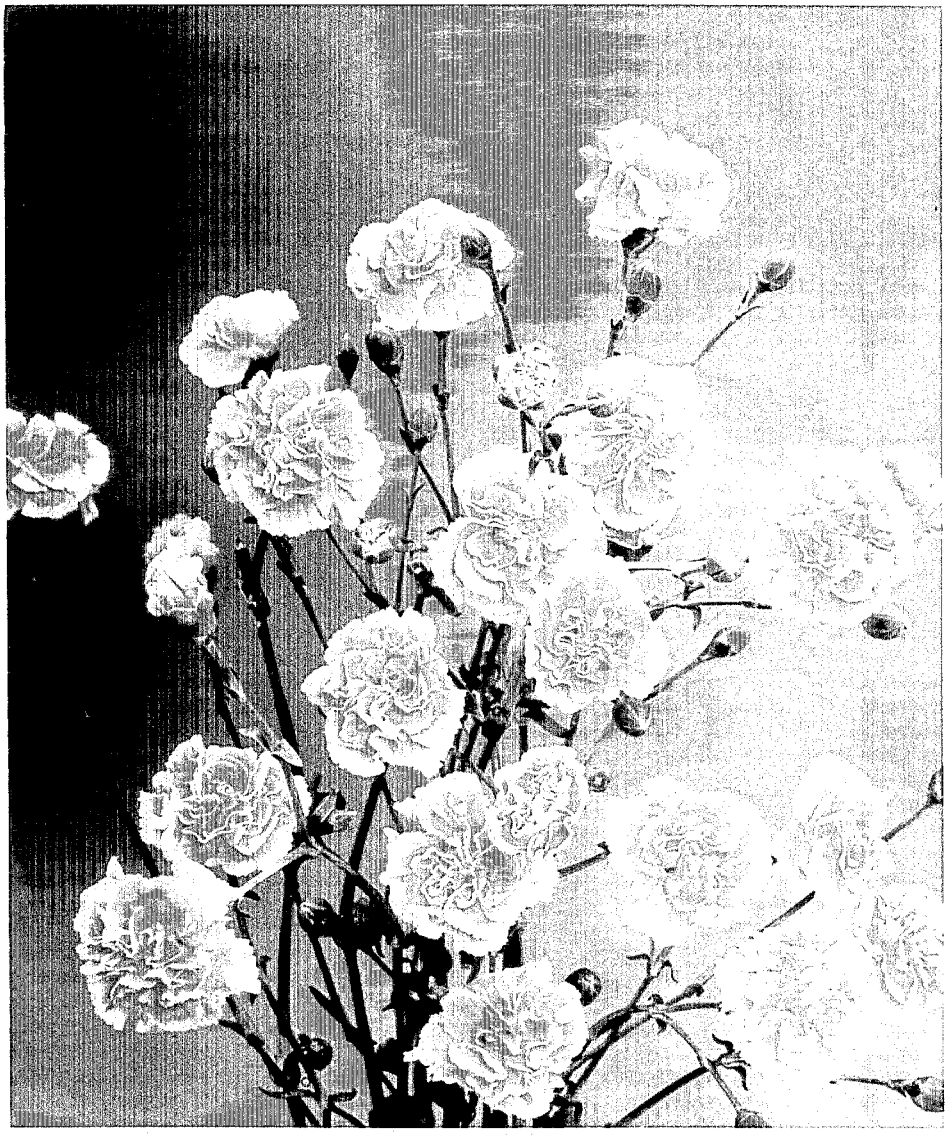

* * * * *